(12) United States Patent
Hegde et al.

(10) Patent No.: US 7,198,595 B2
(45) Date of Patent: Apr. 3, 2007

(54) CARDIAC APPARATUS INCLUDING ELECTROACTIVE POLYMER ACTUATORS AND METHODS OF USING THE SAME

(75) Inventors: Anant V. Hegde, Newark, CA (US); Wally S. Buch, Atherton, CA (US); Halil I. Karabey, San Jose, CA (US)

(73) Assignee: Pavad Medical, Inc., Fremont, CA (US)

( * ) Notice: Subject to any disclaimer, the term of this patent is extended or adjusted under 35 U.S.C. 154(b) by 38 days.

(21) Appl. No.: 10/810,134

(22) Filed: Mar. 26, 2004

(65) Prior Publication Data

US 2004/0249236 A1 Dec. 9, 2004

Related U.S. Application Data

(60) Provisional application No. 60/457,666, filed on Mar. 26, 2003.

(51) Int. Cl.
*A61N 1/362* (2006.01)
(52) U.S. Cl. ....................................................... 600/16
(58) Field of Classification Search ............ 600/16–18, 600/30, 37
See application file for complete search history.

(56) References Cited

U.S. PATENT DOCUMENTS

| | | | | |
|---|---|---|---|---|
| 6,126,590 A * | 10/2000 | Alferness | ..................... | 600/37 |
| 6,169,922 B1 * | 1/2001 | Alferness et al. | ............... | 607/5 |
| 6,464,655 B1 | 10/2002 | Shahinpoor | | |
| 6,749,556 B2 * | 6/2004 | Banik | ........................... | 600/30 |
| 6,809,462 B2 * | 10/2004 | Pelrine et al. | ............... | 310/319 |
| 2004/0010180 A1 | 1/2004 | Scorvo | | |
| 2004/0167375 A1 * | 8/2004 | Couvillon | ..................... | 600/17 |

* cited by examiner

*Primary Examiner*—Robert E. Pezzuto
*Assistant Examiner*—Jessica L. Reidel
(74) *Attorney, Agent, or Firm*—James R. Shay; Shay Law Group LLP

(57) ABSTRACT

Cardiac apparatus and methods of using such cardiac apparatus are described. In one embodiment, a cardiac apparatus includes a covering that is configured to at least partially encircle a heart with a first portion of the covering adjacent to a second portion of the covering. The cardiac apparatus also includes an electroactive polymer actuator. A first end of the electroactive polymer actuator is coupled to the first portion of the covering, and a second end of the electroactive polymer actuator is coupled to the second portion of the covering. The second end of the electroactive polymer actuator is oriented such that, upon actuation of the electroactive polymer actuator, the second end of the electroactive polymer actuator extends away from the first end of the electroactive polymer actuator to move the second portion of the covering towards the first portion of the covering.

22 Claims, 6 Drawing Sheets

CARDIAC APPARATUS INCLUDING ELECTROACTIVE POLYMER ACTUATORS AND METHODS OF USING THE SAME

CROSS-REFERENCE TO RELATED APPLICATION

This application claims the benefit of U.S. Provisional Application No. 60/457,666, entitled "Electroactive Polymeric (EAP) Epicardial Sock" and filed on Mar. 26, 2003, the disclosure of which is incorporated herein by reference in its entirety.

FIELD OF THE INVENTION

The invention relates to cardiac apparatus and methods. For example, cardiac apparatus including electroactive polymer actuators and methods of using such cardiac apparatus are described.

BACKGROUND OF THE INVENTION

Congestive heart failure is a debilitating and progressive disease that causes a heart to pump less efficiently over time. Typically, the heart has been weakened by an underlying problem, such as clogged arteries, high blood pressure, a defect in heart muscles or heart valves, or some other medical condition. The progression of congestive heart failure is often caused by the heart's own efforts to compensate for weakening of the heart. In particular, portions of the heart, particularly the ventricles, can become increasingly enlarged as the heart tries to compensate for weakening of the heart muscles. As the heart enlarges, the heart performs an increasing amount of work to supply blood through the vasculature of a body. Over time, the heart can become so enlarged that the heart can no longer provide an adequate supply of blood to the body. As a result, individuals afflicted with congestive heart failure often experience shortness of breath and fatigue even when performing simple daily activities. Moreover, as the heart enlarges, the heart valves may not adequately close, thus further reducing the heart's ability to supply blood to the body.

Drug therapies have been developed to treat individuals afflicted with congestive heart failure. Existing drug therapies can alleviate the symptoms of congestive heart failure and can sometimes slow the progression of congestive heart failure. However, existing drug therapies typically are unable to halt or reverse the progression of congestive heart failure. Moreover, existing drug therapies can sometimes produce adverse side effects. Surgical procedures have also been developed to treat congestive heart failure. Examples of existing surgical procedures include the Batista procedure and cardiomyoplasty. However, such existing surgical procedures can be invasive, risky, and expensive while providing limited improvements in cardiac performance.

In light of the shortcomings of existing drug therapies and existing surgical procedures, attempts have been made to treat congestive heart failure with cardiac jackets. An existing cardiac jacket can be fitted to an enlarged heart to limit expansion of the heart during diastole. While an existing cardiac jacket can impede further enlargement of the heart, such cardiac jacket is typically a passive device that does not provide active assistance to the heart during systole. Moreover, the size of an existing cardiac jacket typically cannot be readily adjusted over time to reverse the enlargement of the heart. In particular, once an existing cardiac jacket is implanted within a body, adjusting the size of such cardiac jacket typically requires further surgical procedures, which can be invasive, risky, and expensive.

It is against this background that a need arose to develop the cardiac apparatus and methods described herein.

SUMMARY OF THE INVENTION

In one innovative aspect, the invention relates to a cardiac apparatus. In one embodiment, the cardiac apparatus includes a covering including a first portion and a second portion. The covering is configured to at least partially encircle a heart with the first portion of the covering adjacent to the second portion of the covering. The cardiac apparatus also includes an electroactive polymer actuator including a first end and a second end. The first end of the electroactive polymer actuator is coupled to the first portion of the covering, and the second end of the electroactive polymer actuator is coupled to the second portion of the covering. The second end of the electroactive polymer actuator is oriented such that, upon actuation of the electroactive polymer actuator, the second end of the electroactive polymer actuator extends away from the first end of the electroactive polymer actuator to move the second portion of the covering towards the first portion of the covering.

In another embodiment, the cardiac apparatus includes a covering including a first portion and a second portion spaced apart from the first portion. The covering has a size to at least partially surround a heart. The cardiac apparatus also includes a size adjustment mechanism coupled to the covering and configured to adjust the size of the covering. The size adjustment mechanism includes a multi-layered electroactive polymer actuator including a first end and an opposite, second end. The first end of the multi-layered electroactive polymer actuator is coupled to the first portion of the covering. The size adjustment mechanism also includes a coupling member including a first end and an opposite, second end. The first end of the coupling member is coupled to the second end of the multi-layered electroactive polymer actuator, and the second end of the coupling member is coupled to the second portion of the covering.

In a further embodiment, the cardiac apparatus includes a covering configured to at least partially surround a heart. The cardiac apparatus also includes a size adjustment mechanism coupled to the covering. The size adjustment mechanism includes an electroactive polymer actuator configured to expand upon actuation to compress the heart.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of various embodiments of the invention, reference should be made to the following detailed description taken in conjunction with the accompanying drawings.

DETAILED DESCRIPTION

Embodiments of the invention provide improved cardiac apparatus and methods that can be used to treat congestive heart failure with greater efficacy. In particular, some embodiments of the invention provide a cardiac apparatus that can be fitted to an enlarged heart to impede further enlargement of the heart. Advantageously, the cardiac apparatus includes a set of electroactive polymer actuators that can be actuated to adjust the size of the cardiac apparatus. For certain implementations, the set of electroactive polymer actuators can be actuated based on a cardiac cycle of the heart, such that the cardiac apparatus provides active assistance to the heart to supply blood to a body. For other implementations, the set of electroactive polymer actuators can be actuated on a periodic basis or a non-periodic basis, such that the size of the cardiac apparatus is gradually adjusted over time to reverse the enlargement of the heart. Accordingly, the size of the cardiac apparatus can be readily adjusted following implantation without requiring further surgical procedures.

Figure 1:
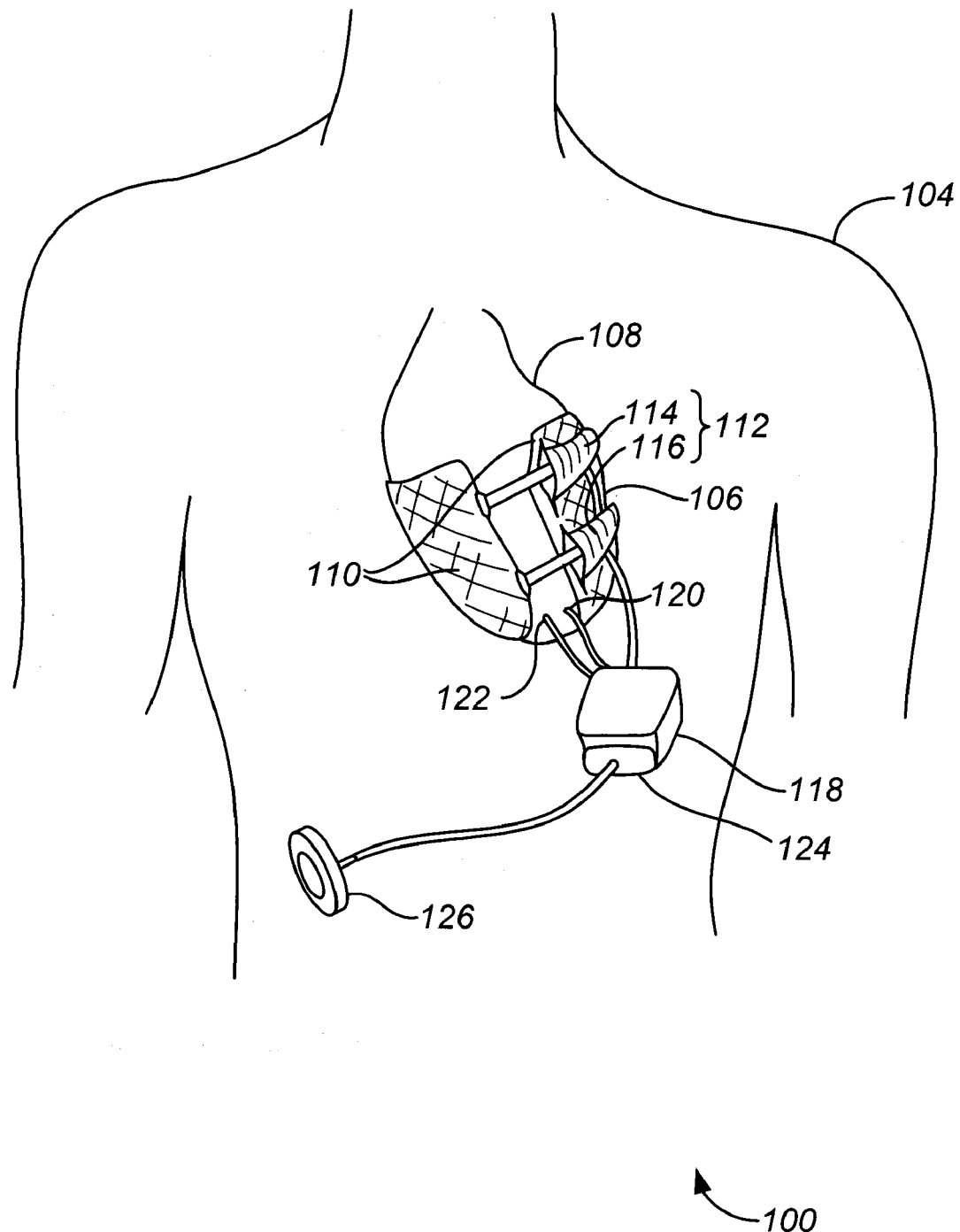
FIG. 1 illustrates a cardiac apparatus that can be used to treat congestive heart failure according to an embodiment of the invention.

FIG. 1 illustrates a cardiac apparatus 100 that can be used to treat congestive heart failure according to an embodiment of the invention. In the illustrated embodiment, the cardiac apparatus 100 includes a number of components that are implantable within a body 104.

As illustrated in FIG. 1, the cardiac apparatus 100 includes a cardiac constraint device 106, which is fitted to a heart 108 to impede expansion of the heart 108 during diastole. The cardiac constraint device 106 includes a covering 110, which is configured to at least partially surround the heart 108 to impede further enlargement of the heart 108. The covering 110 can be formed from any of a number of biologically compatible materials, including, for example, polyester, polyethylene, polytetrafluoroethylene, and polypropylene. For certain implementations, the covering 110 can be formed in a knit pattern or a mesh pattern. Such knit pattern or mesh pattern can serve to provide desired mechanical properties to the covering 110, including, for example, a desired level of flexibility. In addition, such knit pattern or mesh pattern can define interstitial spaces or openings that allow a desired level of fluid permeability as well as reduce the amount of surface area in contact with the heart 108, thus reducing the possibility of irritation or abrasion of the heart 108.

As illustrated in FIG. 1, the cardiac constraint device 106 also includes a size adjustment mechanism 112, which is coupled to the covering 110 and is configured to adjust the circumferential size of the covering 110. In the illustrated embodiment, the size adjustment mechanism 112 includes a pair of electroactive polymer actuators 114 and 116. The electroactive polymer actuators 114 and 116 are configured to undergo deflection upon actuation to adjust the circumferential size of the covering 110. In general, deflection refers to any displacement, expansion, contraction, torsion, linear strain, area strain, or other deformation. While two electroactive polymer actuators 114 and 116 are illustrated in FIG. 1, it is contemplated that more or less electroactive polymer actuators can be included depending on the particular implementation. In the illustrated embodiment, the electroactive polymer actuators 114 and 116 are actuated based on a cardiac cycle of the heart 108, such that the cardiac constraint device 106 provides active assistance to the heart 108 to supply blood to the body 104. Alternatively, or in conjunction, the size adjustment mechanism 112 can allow a particular circumferential size of the covering 110 to be retained following actuation of the electroactive polymer actuators 114 and 116, such that the circumferential size of the covering 110 is gradually adjusted over time to reverse the enlargement of the heart 108.

Figure 2A:
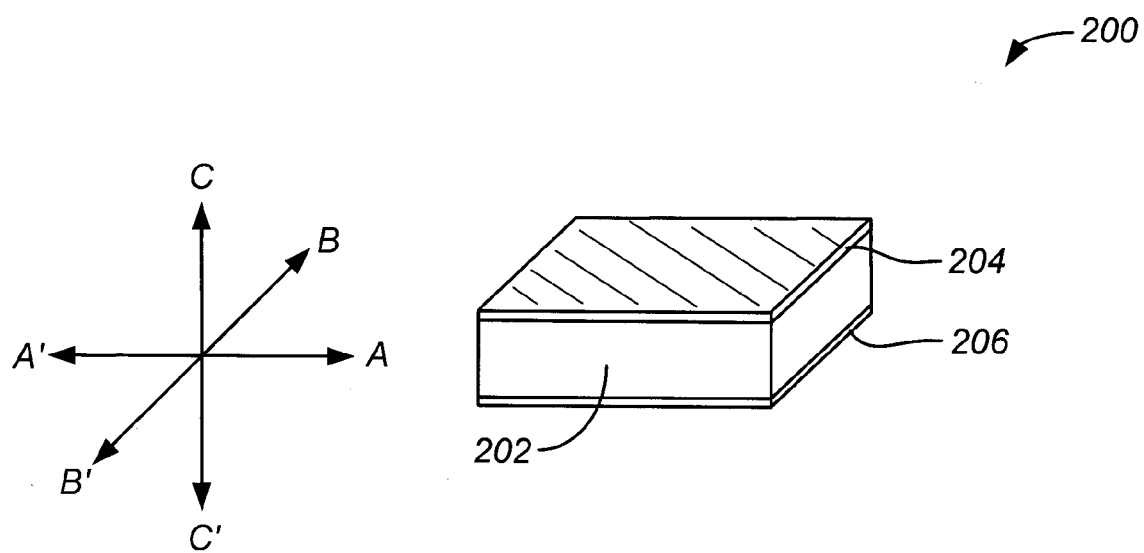
FIG. 2A and FIG. 2B illustrate perspective views of an electroactive polymer actuator in a non-actuated state and an actuated state, respectively, according to an embodiment of the invention.
Figure 2B:
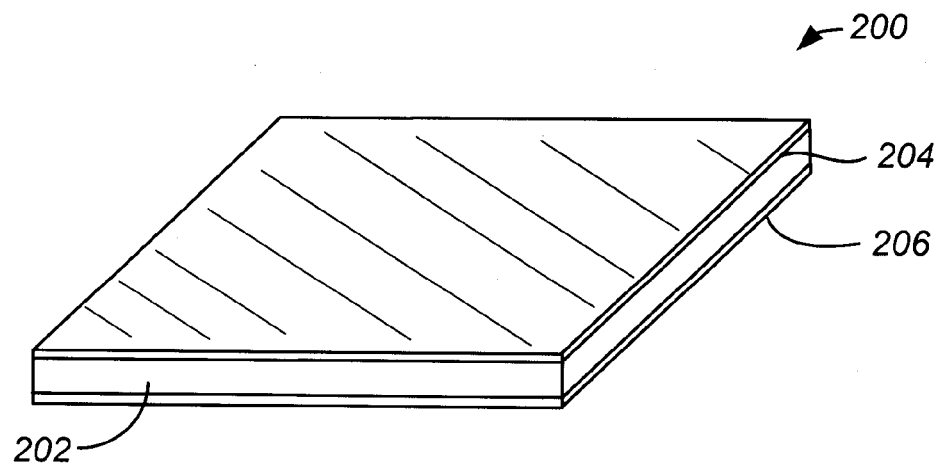

In the illustrated embodiment, the electroactive polymer actuators 114 and 116 are configured to undergo deflection upon application of electrical energy. Such deflection is illustrated in FIG. 2A and FIG. 2B, which provide perspective views of an electroactive polymer actuator 200 according to an embodiment of the invention. In particular, FIG. 2A and FIG. 2B illustrate the electroactive polymer actuator 200 in a non-actuated state and an actuated state, respectively.

As illustrated in FIG. 2A, the electroactive polymer actuator 200 has a generally planar shape and includes an elastomeric polymer layer 202 positioned between a pair of electrodes 204 and 206. In the illustrated embodiment, the elastomeric polymer layer 202 is configured to deflect when a voltage difference is applied across the elastomeric polymer layer 202. The electroactive polymer actuator 200 can be formed from any of a number of polymers, including, for example, dielectric electrostrictive electroactive polymers, ion-exchange electroactive polymers, and ionomeric polymer-metal composite electroactive polymers. For certain implementations, dielectric electrostrictive electroactive polymers are particularly desirable because of their faster response times and greater operational efficiencies. Specific examples of polymers that can be used include Nusil CF19-2186 (available from Nusil Technology, Carpenteria, Calif.); dielectric elastomeric polymers; silicone rubbers; silicone elastomers; acrylic elastomers, such as VHB 4910 acrylic elastomer (available from 3M Corporation, St. Paul, Minn.); silicones, such as Dow Corning HS3 (available from Dow Corning, Wilmington, Del.); fluorosilicones, such as Dow Corning 730 (available from Dow Corning, Wilmington, Del.); acrylic polymers, such as acrylics in the 4900 VHB acrylic series (available from 3M Corporation, St. Paul, Minn.); polyurethanes; thermoplastic elastomers; copolymers including poly(vinylidene fluoride); pressure-sensitive adhesives; fluoroelastomers; polymers including silicone and acrylics, such as copolymers including silicone and acrylic and polymer blends including a silicone elastomer and an acrylic elastomer; and combinations of two or more of these polymers.

As illustrated in FIG. 2A, the electrodes 204 and 206 are attached to top and bottom surfaces of the elastomeric polymer layer 202 to allow a voltage difference to be applied across the elastomeric polymer layer 202. In the illustrated embodiment, the electrodes 204 and 206 are compliant, such that the electrodes 204 and 206 deflect along with the elastomeric polymer layer 202 during actuation. The electrodes 204 and 206 can be formed from any of a number of electrically conductive materials, including, for example, graphite; carbon black; metals, such as gold, platinum, and silver; silver-filled gels and polymers; carbon-filled gels and polymers; electrically conductive polymers; and combinations of two or more of these electrically conductive materials.

In the illustrated embodiment, actuation of the electroactive polymer actuator 200 causes it to deflect to a thinner, larger area shape as illustrated in FIG. 2B. In particular, when a voltage difference is applied to the electrodes 204 and 206, the elastomeric polymer layer 202 expands along planar directions A and A' and along planar directions B and B'. In the illustrated embodiment, the elastomeric polymer layer 202 is substantially incompressible, such that the volume of the elastomeric polymer layer 202 remains substantially constant under deflection. Accordingly, as the elastomeric polymer layer 202 expands along the planar directions A, A', B, and B', the elastomeric polymer layer 202 contracts between the electrodes 204 and 206 along vertical directions C and C' to decrease the thickness of the electroactive polymer actuator 200. During actuation, the electroactive polymer actuator 200 can continue to deflect until mechanical forces balance electrical forces driving the deflection. The mechanical forces can include, for example, elastic restoring forces of the elastomeric polymer layer 202, compliance of the electrodes 204 and 206, and any external resistance or load provided to the electroactive polymer actuator 200. The degree of deflection of the electroactive polymer actuator 200 as a result of an applied voltage difference can also depend on a number of other factors, such as a dielectric constant of the elastomeric polymer layer 202 and the size of the elastomeric polymer layer 202.

Subsequent to actuation, the electroactive polymer actuator 200 reverts back to a thicker, smaller area shape as illustrated in FIG. 2A. In particular, once the voltage difference is no longer applied to the electrodes 204 and 206, the elastomeric polymer layer 202 contracts along the planar directions A and A' and along the planar directions B and B'. As discussed previously, the elastomeric polymer layer 202 is substantially incompressible. Accordingly, as the elastomeric polymer layer 202 contracts along the planar directions A, A', B, and B', the elastomeric polymer layer 202 expands between the electrodes 204 and 206 along the vertical directions C and C' to increase the thickness of the electroactive polymer actuator 200.

Figure 3A:
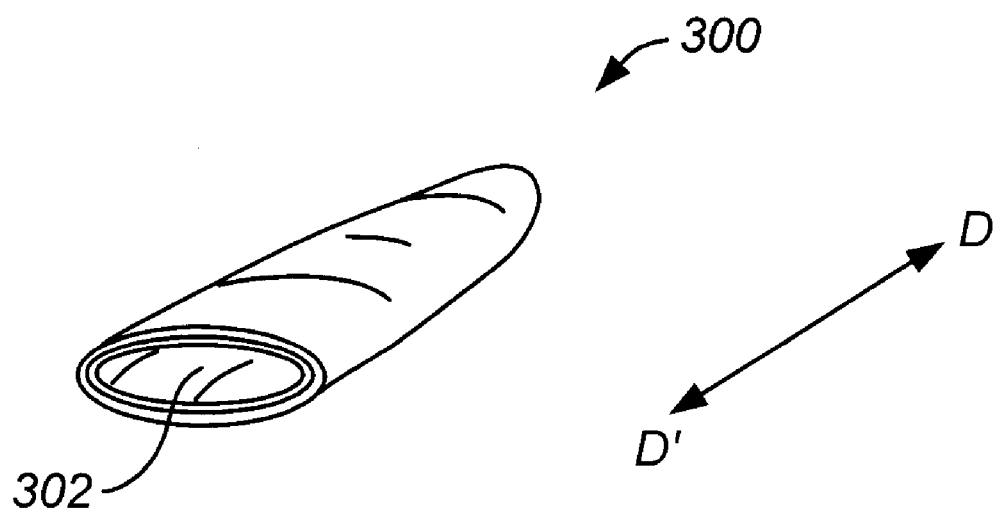
FIG. 3A and FIG. 3B illustrate perspective, cross-sectional views of a multi-layered electroactive polymer actuator in a non-actuated state and an actuated state, respectively, according to an embodiment of the invention.
Figure 3B:
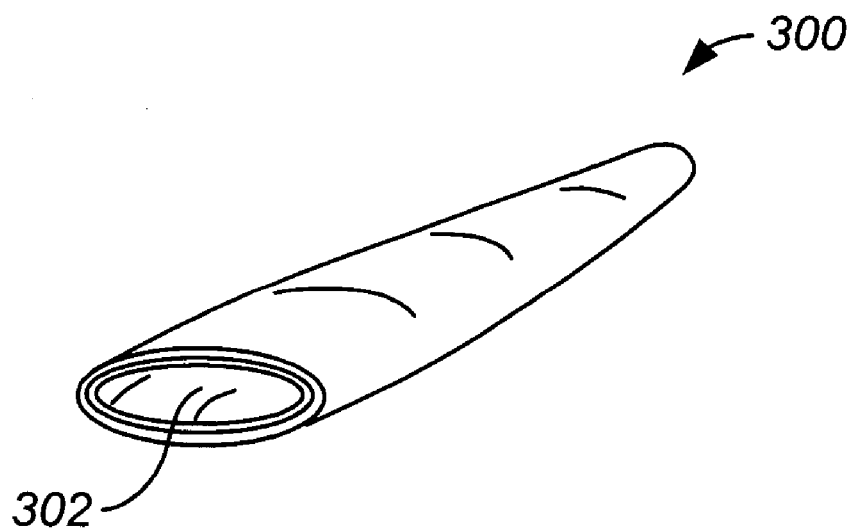

While the electroactive polymer actuator 200 is illustrated as having a generally planar shape, it is contemplated that electroactive polymer actuators can have any of a number of other shapes. FIG. 3A and FIG. 3B illustrate perspective, cross-sectional views of a multi-layered electroactive polymer actuator 300 according to an embodiment of the invention. In particular, FIG. 3A and FIG. 3B illustrate the multi-layered electroactive polymer actuator 300 in a non-actuated state and an actuated state, respectively.

As illustrated in FIG. 3A, the multi-layered electroactive polymer actuator 300 has a generally tubular shape and defines an interior cavity 302 that extends at least partly through the length of the multi-layered electroactive polymer actuator 300. The multi-layered electroactive polymer actuator 300 can be formed by, for example, rolling an electroactive polymer actuator having a generally planar shape (e.g., the electroactive polymer actuator 200) onto itself or around an object.

In the illustrated embodiment, actuation of the multi-layered electroactive polymer actuator 300 causes it to deflect to a longer shape as illustrated in FIG. 3B. In particular, when a voltage difference is applied, the multi-layered electroactive polymer actuator 300 expands along axial directions D and D'. In conjunction, the multi-layered electroactive polymer actuator 300 can deflect circumferentially to have a larger or smaller cross-sectional area. Subsequent to actuation, the multi-layered electroactive polymer actuator 300 reverts back to a shorter shape as illustrated in FIG. 3A. In particular, once the voltage difference is no longer applied, the multi-layered electroactive polymer actuator 300 contracts along the axial directions D and D'.

Referring back to FIG. 1, the cardiac apparatus 100 also includes a controller 118, which is electrically coupled to the size adjustment mechanism 112 and is configured to control operation of the size adjustment mechanism 112. In the illustrated embodiment, the controller 118 actuates the electroactive polymer actuators 114 and 116 based on a cardiac cycle of the heart 108, such that the cardiac constraint device 106 provides active assistance to the heart 108 by compressing the heart 108 during systole. Alternatively, or in conjunction, the controller 118 can actuate the electroactive polymer actuators 114 and 116 on a periodic basis or a non-periodic basis, such that the circumferential size of the covering 110 can be gradually adjusted over time to reverse the enlargement of the heart 108. Accordingly, the circumferential size of the covering 110 can be readily adjusted following implantation without requiring further surgical procedures. It is contemplated that the controller 118 can selectively actuate one of the electroactive polymer actuators 114 and 116 at a particular time or can actuate the electroactive polymer actuators 114 and 116 at different actuation levels. Such selective or differential actuation of the electroactive polymer actuators 114 and 116 can serve to provide improved active assistance to the heart 108 by, for example, coordinating actuation of the electroactive polymer actuators 114 and 116 with the flow of blood through the heart 108. Alternatively, or in conjunction, such selective or differential actuation of the electroactive polymer actuators 114 and 116 can provide greater control over the circumferential size of the covering 110 along the length of the heart 108, thus allowing the heart 108 to be reshaped to a normal condition. The controller 118 can be implemented using, for example, dedicated hardware or logic elements configured as a programmable gate array or a typical microprocessor or central processing unit.

In the illustrated embodiment, the cardiac apparatus 100 also includes a pair of sensors 120 and 122, which are electrically coupled to the controller 118. The sensors 120 and 122 are configured to detect a signal representing a cardiac cycle of the heart 108. Such signal can be, for example, a signal representing a cardiac rhythm or a blood pressure, such as in the aorta, the vena cava, or any other blood vessel in the body 104. During operation of the cardiac apparatus 100, the controller 118 receives the signal representing the cardiac cycle detected by the sensors 120 and 122 and actuates the electroactive polymer actuators 114 and 116 based on that signal. The sensors 120 and 122 can be implemented using, for example, electrical sensors, such as electrocardiogram leads, or pressure sensors, such as pressure gauges, pressure catheters, and pressure transducers.

As illustrated in FIG. 1, the cardiac apparatus 100 also includes a power source 124, which is electrically coupled to the controller 118 and is configured to provide power to various components of the cardiac apparatus 100. The power source 124 can be implemented using, for example, a battery, such as a rechargeable battery. In the illustrated embodiment, the cardiac apparatus 100 further includes a transducer 126, which is electrically coupled to the power source 124 and is configured to allow the power source 124 to be recharged transcutaneously. Alternatively, or in conjunction, the transducer 126 can be electrically coupled to the controller 118 and can be configured to allow transcutaneous transfer of control signals to direct operation of the controller 118. For example, such control signals can be provided on a periodic basis or a non-periodic basis to direct the controller 118 to actuate the electroactive polymer actuators 114 and 116. The transducer 126 can also be configured to allow transcutaneous transfer of data signals to allow monitoring of the operation of the cardiac apparatus 100 or monitoring of cardiac performance.

Figure 4:
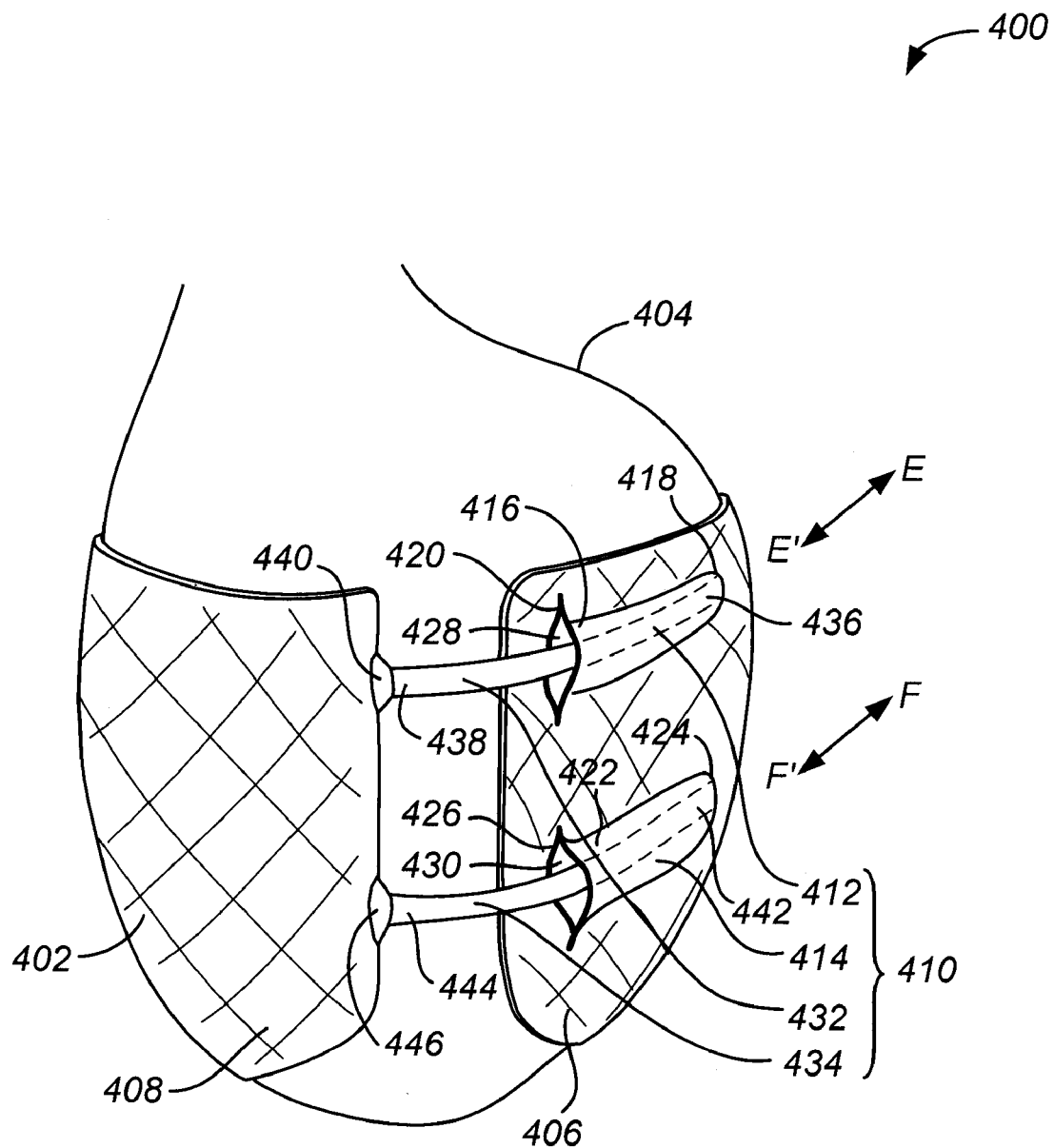
FIG. 4 illustrates a cardiac constraint device according to an embodiment of the invention.

Attention next turns to FIG. 4, which illustrates a cardiac constraint device 400 according to an embodiment of the invention. The cardiac constraint device 400 includes a covering 402, which is configured to at least partially encircle a heart 404. In particular, the covering 402 is configured to at least partially encircle the ventricles of the heart 404 to impede further enlargement of the ventricles. In the illustrated embodiment, the covering 402 has an elongated shape and includes a first end portion 406 and a second end portion 408. As illustrated in FIG. 4, the cardiac constraint device 400 is fitted to the heart 404, such that the first end portion 406 of the covering 402 is adjacent to the second end portion 408 of the covering 402.

The cardiac constraint device 400 also includes a size adjustment mechanism 410, which is coupled to the covering 402 and is configured to adjust the circumferential size of the covering 402. In the illustrated embodiment, the size adjustment mechanism 410 includes a pair of multi-layered electroactive polymer actuators 412 and 414. The multi-layered electroactive polymer actuator 412 includes a first end 416 and an opposite, second end 418. The first end 416 of the multi-layered electroactive polymer actuator 412 is coupled to the first end portion 406 of the covering 402 via a retaining member 420. As illustrated in FIG. 4, the multi-layered electroactive polymer actuator 412 has a generally tubular shape and defines an interior cavity 428 that extends at least partly through the length of the multi-layered electroactive polymer actuator 412. Similarly, the multi-layered electroactive polymer actuator 414 includes a first end 422 and an opposite, second end 424. The first end 422 of the multi-layered electroactive polymer actuator 414 is coupled to the first end portion 406 of the covering 402 via a retaining member 426. As illustrated in FIG. 4, the multi-layered electroactive polymer actuator 414 has a generally tubular shape and defines an interior cavity 430 that extends at least partly through the length of the multi-layered electroactive polymer actuator 414.

In the illustrated embodiment, the size adjustment mechanism 410 also includes a pair of coupling members 432 and 434. The coupling members 432 and 434 include portions that extend through respective ones of the interior cavity 428 and the interior cavity 430, which portions are illustrated using dashed lines in FIG. 4. As illustrated in FIG. 4, the coupling member 432 includes a first end 436 and an opposite, second end 438. The first end 436 of the coupling member 432 is coupled to the second end 418 of the multi-layered electroactive polymer actuator 412 within the interior cavity 428, and the second end 438 of the coupling member 432 is coupled to the second end portion 408 of the covering 402 via a retaining member 440. Similarly, the coupling member 434 includes a first end 442 and an opposite, second end 444. The first end 442 of the coupling member 434 is coupled to the second end 424 of the multi-layered electroactive polymer actuator 414 within the interior cavity 430, and the second end 444 of the coupling member 434 is coupled to the second end portion 408 of the covering 402 via a retaining member 446.

As illustrated in FIG. 4, the second end 418 of the multi-layered electroactive polymer actuator 412 is oriented such that, upon actuation of the multi-layered electroactive polymer actuator 412, the second end 418 of the multi-layered electroactive polymer actuator 412 extends away from the first end 416 of the multi-layered electroactive polymer actuator 412 along direction E. Such extension of the second end 418 of the multi-layered electroactive polymer actuator 412 causes the coupling member 432 to move along the direction E, which, in turn, causes the second end portion 408 of the covering 402 to move towards the first end portion 406 of the covering 402. Subsequent to actuation of the multi-layered electroactive polymer actuator 412, the second end 418 of the multi-layered electroactive polymer actuator 412 contracts towards the first end 416 of the multi-layered electroactive polymer actuator 412 along direction E'. Such contraction of the second end 418 of the multi-layered electroactive polymer actuator 412 causes the coupling member 432 to move along the direction E', which, in turn, causes the second end portion 408 of the covering 402 to move away from the first end portion 406 of the covering 402.

Similarly, the second end 424 of the multi-layered electroactive polymer actuator 414 is oriented such that, upon actuation of the multi-layered electroactive polymer actuator 414, the second end 424 of the multi-layered electroactive polymer actuator 414 extends away from the first end 422 of the multi-layered electroactive polymer actuator 414 along direction F. Such extension of the second end 424 of the multi-layered electroactive polymer actuator 414 causes the coupling member 434 to move along the direction F, which, in turn, causes the second end portion 408 of the covering 402 to move towards the first end portion 406 of the covering 402. Subsequent to actuation of the multi-layered electroactive polymer actuator 414, the second end 424 of the multi-layered electroactive polymer actuator 414 contracts towards the first end 422 of the multi-layered electroactive polymer actuator 414 along direction F'. Such contraction of the second end 424 of the multi-layered electroactive polymer actuator 414 causes the coupling member 434 to move along the direction F', which, in turn, causes the second end portion 408 of the covering 402 to move away from the first end portion 406 of the covering 402.

In the illustrated embodiment, by repeatedly actuating either, or both, of the multi-layered electroactive polymer actuators 412 and 414, the circumferential size of the covering 402 can be adjusted to be substantially synchronized with a pumping action of the heart 404. In particular, actuation of the multi-layered electroactive polymer actuators 412 and 414 can be coordinated based on a cardiac cycle of the heart 404, such that the cardiac constraint device 400 provides active assistance to the heart 404 by compressing the heart 404 during systole and expanding during diastole to allow the heart 404 to fill with blood.

To allow the circumferential size of the covering 402 to be readily adjusted following implantation, portions of the covering 402 can be coated with any of a number of growth-retarding materials, including, for example, Hyaluronan. For certain implementations, portions of the cardiac constraint device 400 can be secured to the heart 404 to prevent undesirable shifting following implantation. For example, the cardiac constraint device 400 can be secured to the heart 404 using sutures or staples.

Figure 5:
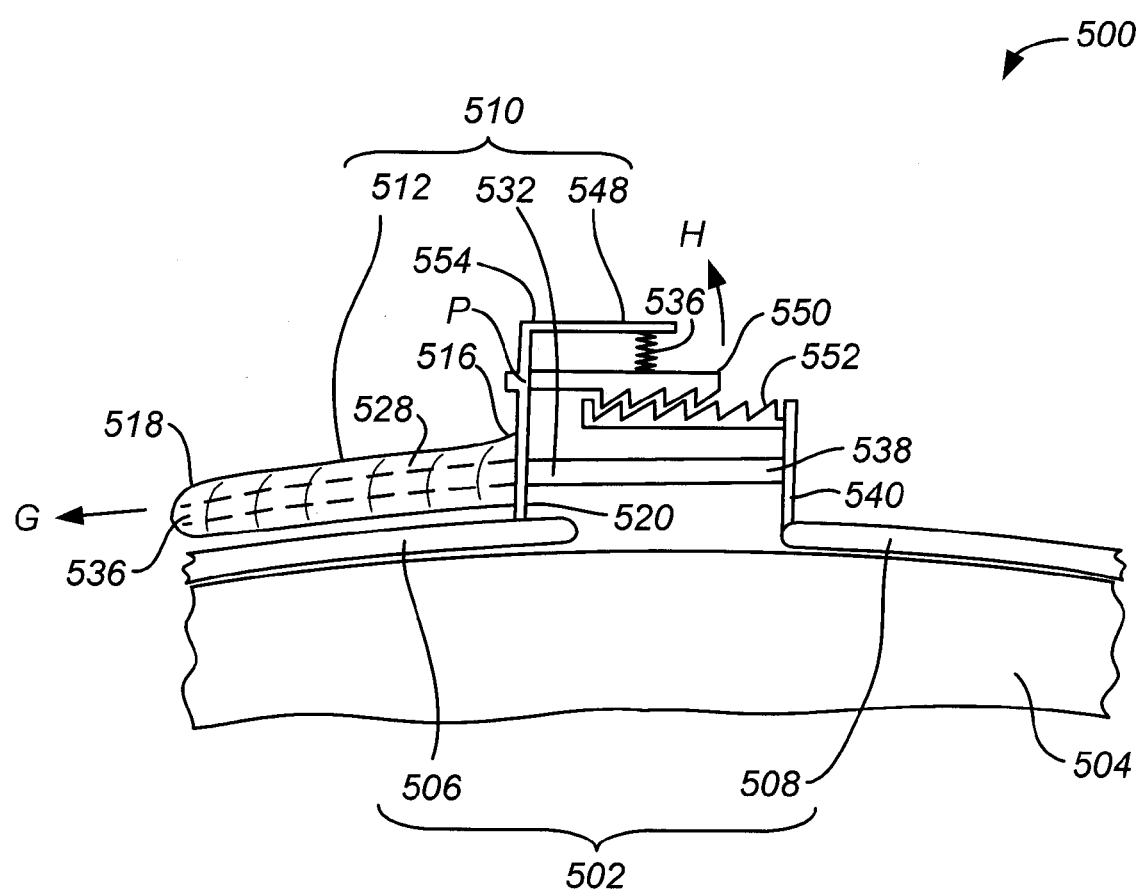
FIG. 5 illustrates a top, sectional view of a cardiac constraint device according to another embodiment of the invention.

FIG. 5 illustrates a top, sectional view of a cardiac constraint device 500 according to another embodiment of the invention. The cardiac constraint device 500 includes a covering 502, which is configured to at least partially encircle a heart 504. In the illustrated embodiment, the covering 502 includes a first end portion 506 and a second end portion 508. As illustrated in FIG. 5, the cardiac constraint device 500 is fitted to the heart 504, such that the first end portion 506 of the covering 502 is adjacent to the second end portion 508 of the covering 502.

The cardiac constraint device 500 also includes a size adjustment mechanism 510, which is coupled to the covering 502 and is configured to adjust the circumferential size of the covering 502. In the illustrated embodiment, the size adjustment mechanism 510 includes a multi-layered electroactive polymer actuator 512. The multi-layered electroactive polymer actuator 512 includes a first end 516 and an opposite, second end 518. The first end 516 of the multi-layered electroactive polymer actuator 512 is coupled to the first end portion 506 of the covering 502 via a retaining member 520. As illustrated in FIG. 5, the multi-layered electroactive polymer actuator 512 has a generally tubular shape and defines an interior cavity 528 that extends at least partly through the length of the multi-layered electroactive polymer actuator 512.

In the illustrated embodiment, the size adjustment mechanism 510 also includes a coupling member 532. The coupling member 532 includes a portion that extends through the interior cavity 528, which portion is illustrated using dashed lines in FIG. 5. As illustrated in FIG. 5, the coupling member 532 includes a first end 536 and an opposite, second end 538. The first end 536 of the coupling member 532 is coupled to the second end 518 of the multi-layered electroactive polymer actuator 512 within the interior cavity 528, and the second end 538 of the coupling member 532 is coupled to the second end portion 508 of the covering 502 via a retaining member 540.

In the illustrated embodiment, the size adjustment mechanism 510 also includes a releasable latch member 548. The releasable latch member 548 is coupled to the first end portion 506 of the covering 502 and the second end portion 508 of the covering 502 and is configured to retain the first end portion 506 of the covering 502 at a particular spacing with respect to the second end portion 508 of the covering 502. As illustrated in FIG. 5, the releasable latch member 548 includes a pair of sawtooth members 550 and 552. The sawtooth member 550 is coupled to the retaining member 520 via an extension 554, and the sawtooth member 552 is coupled to the retaining member 540. In the illustrated embodiment, the sawtooth member 550 is configured to pivot about pivot point P with respect to the extension 554, and a spring 556 is included to apply a downward biasing force on the sawtooth member 550.

As illustrated in FIG. 5, the second end 518 of the multi-layered electroactive polymer actuator 512 is oriented such that, upon actuation of the multi-layered electroactive polymer actuator 512, the second end 518 of the multi-layered electroactive polymer actuator 512 extends away from the first end 516 of the multi-layered electroactive polymer actuator 512 along direction G. Such extension of the second end 518 of the multi-layered electroactive polymer actuator 512 causes the coupling member 532 to move along the direction G, which, in turn, causes the second end portion 508 of the covering 502 to move towards the first end portion 506 of the covering 502. In conjunction, the sawtooth member 550 pivots along direction H to allow a next "tooth" of the sawtooth member 552 to be engaged. Once this next "tooth" is engaged, the downward biasing force applied by the spring 556 locks the sawtooth members 550 and 552 with respect to one another, thus retaining the first end portion 506 of the covering 502 at a desired spacing with respect to the second end portion 508 of the covering 502.

In the illustrated embodiment, by actuating the multi-layered electroactive polymer actuator 512 on a periodic basis or a non-periodic basis, the circumferential size of the covering 502 can be readily adjusted following implantation to allow gradual reshaping of the heart 504 to a normal condition.

Figure 6A:
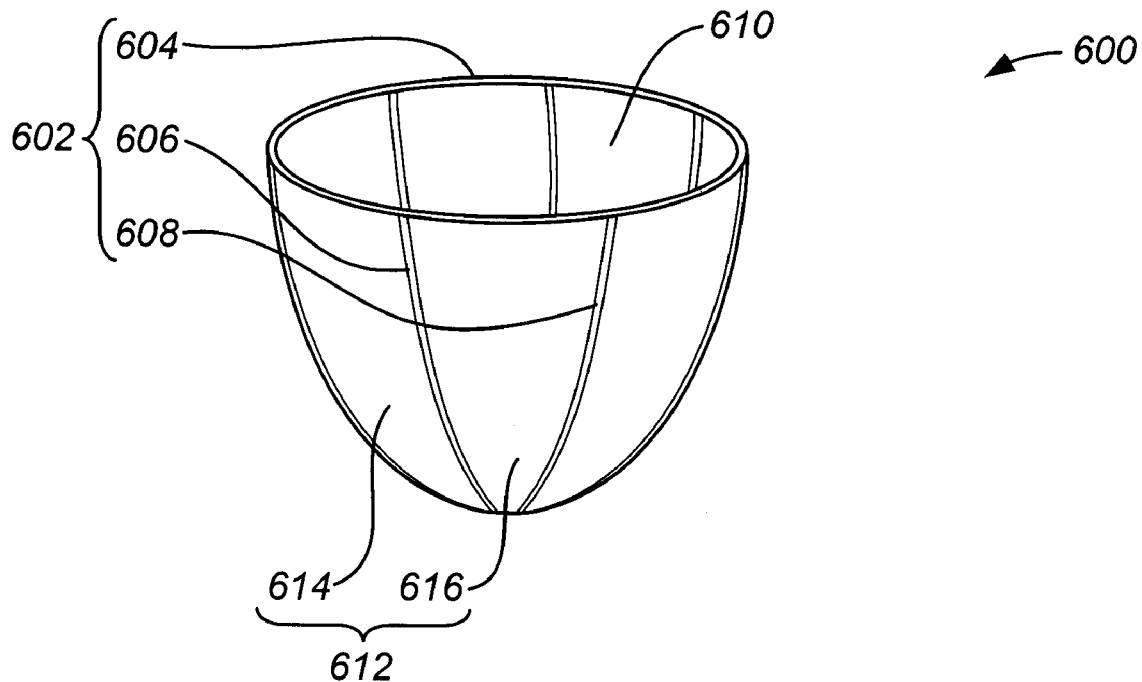
FIG. 6A and FIG. 6B illustrate various views of a cardiac constraint device according to a further embodiment of the invention.
Figure 6B:
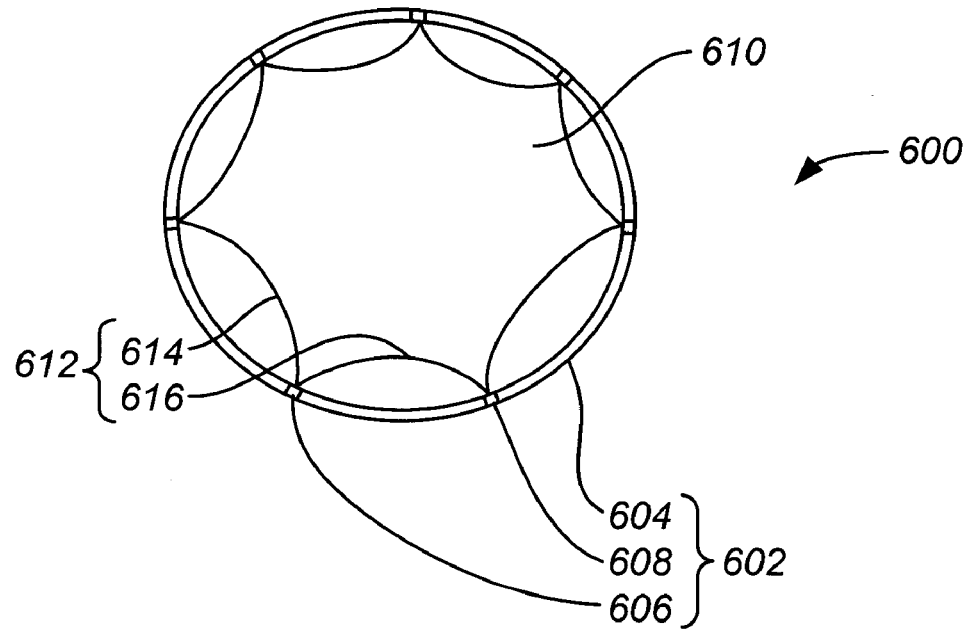

It should be recognized that the embodiments of the invention discussed above are provided by way of example, and various other embodiments are encompassed by the invention. For example, FIG. 6A and FIG. 6B illustrate various views of a cardiac constraint device 600 according to a further embodiment of the invention. In particular, FIG. 6A and FIG. 6B illustrate a perspective view and a top view of the cardiac constraint device 600, respectively.

As illustrated in FIG. 6A, the cardiac constraint device 600 includes a covering 602, which defines an interior cavity 610 within which a heart (not illustrated) can be fitted. In the illustrated embodiment, the covering 602 is formed as a frame that includes a number of support members, such as a circumferential support member 604 and side support members 606 and 608. In the illustrated embodiment, the covering 602 is substantially non-compliant, and two or more of the support members can serve as electrodes. For example, the side support members 606 and 608 can be formed from any of a number of electrically conductive materials and can serve as electrodes to allow a voltage difference to be applied.

The cardiac constraint device 600 also includes a size adjustment mechanism 612, which is coupled to the covering 602 and is configured to adjust the volume of the interior cavity 610. In the illustrated embodiment, the size adjustment mechanism 612 includes a number of electroactive polymer actuators, such as electroactive polymer actuators 614 and 616. As illustrated in FIG. 6A, each of the electroactive polymer actuators has a generally planar shape and is formed as a film that extends between adjacent side support members. For example, the electroactive polymer actuator 616 is formed as a film that extends between the side support members 606 and 608. Upon actuation, the electroactive polymer actuators are configured to expand inwardly to decrease the volume of the interior cavity 610 as illustrated in FIG. 6B. Accordingly, by repeatedly actuating one or more of the electroactive polymer actuators, the volume of the interior cavity 610 can be adjusted to be substantially synchronized with a pumping action of the heart. In particular, actuation of the electroactive polymer actuators can be coordinated based on a cardiac cycle of the heart, such that the cardiac constraint device 600 provides active assistance to the heart by compressing the heart during systole and expanding during diastole to allow the heart to fill with blood.

A practitioner of ordinary skill in the art should require no additional explanation in developing the cardiac apparatus and methods described herein but may nevertheless find some helpful guidance by examining the book of Yoseph Bar-Cohen (Editor), entitled "Electroactive Polymer (EAP) Actuators as Artificial Muscles: Reality, Potential, and Challenges" (2001), the disclosure of which is incorporated herein by reference in its entirety.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, process step or steps, to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A cardiac apparatus, comprising:
   a covering including a first portion and a second portion, said covering being configured to at least partially encircle a heart with said first portion of said covering adjacent to said second portion of said covering; and
   a size adjustment mechanism coupled to said covering, said size adjustment mechanism comprising a coupling member including a first end and a second end and an electroactive polymer actuator including a first end and a second end, said first end of said electroactive polymer actuator being coupled to said first portion of said covering and said first end of said coupling member being coupled to said second end of said electroactive polymer actuator and said second end of said coupling member being coupled to said second portion of said covering, said second end of said electroactive polymer actuator being oriented such that, upon actuation of said electroactive polymer actuator, said second end of said electroactive polymer actuator extends away from said first end of said electroactive polymer actuator to move said second portion of said covering towards said first portion of said covering.

2. The cardiac apparatus of claim 1, wherein said electroactive polymer actuator includes a dielectric electrostrictive electroactive polymer.

3. The cardiac apparatus of claim 1, wherein said electroactive polymer actuator is a multi-layered electroactive polymer actuator.

4. The cardiac apparatus of claim 3, wherein said multi-layered electroactive polymer actuator defines an interior cavity, said coupling member extending through said interior cavity such that said first end of said coupling member is coupled to said second end of said multi-layered electroactive polymer actuator within said interior cavity.

5. The cardiac apparatus of claim 1, further comprising:
   a releasable latch member coupled to said first portion of said covering and said second portion of said covering, said releasable latch member being configured to retain said first portion of said covering at a desired spacing with respect to said second portion of said covering.

6. The cardiac apparatus of claim 5, further comprising:
   a controller electrically coupled to said electroactive polymer actuator, said controller being configured to actuate said electroactive polymer actuator to allow gradual reshaping of said heart.

7. The cardiac apparatus of claim 1, further comprising:
   a sensor configured to detect a cardiac cycle of said heart; and
   a controller electrically coupled to said sensor and to said electroactive polymer actuator, said controller being configured to actuate said electroactive polymer actuator based on said cardiac cycle.

8. The cardiac apparatus of claim 1, wherein said coupling member is a first coupling member and said electroactive polymer actuator is a first electroactive polymer actuator, the cardiac apparatus further comprising a second coupling member including a first end and a second end and a second electroactive polymer actuator including a first end and a second end, said first end of said second electroactive polymer actuator being coupled to said first portion of said covering and said first end of said coupling member being coupled to said second end of said second electroactive polymer actuator and said second end of said second coupling member being coupled to said second portion of said covering, said second end of said second electroactive polymer actuator being oriented such that, upon actuation of said second electroactive polymer actuator, said second end of said second electroactive polymer actuator extends away from said first end of said second electroactive polymer actuator to move said second portion of said covering towards said first portion of said covering.

9. The cardiac apparatus of claim 8, further comprising:
   a controller electrically coupled to said first electroactive polymer actuator and to said second electroactive polymer actuator, said controller being configured to selectively actuate one of said first electroactive polymer actuator and said second electroactive polymer actuator.

10. The cardiac apparatus of claim 8, further comprising:
    a controller electrically coupled to said first electroactive polymer actuator and to said second electroactive polymer actuator, said controller being configured to actuate said first electroactive polymer actuator at a first actuation level and said second electroactive polymer actuator at a second actuation level that is different from said first actuation level.

11. A cardiac apparatus, comprising:
    a covering including a first portion and a second portion spaced apart from said first portion, said covering having a size to at least partially surround a heart; and
    a size adjustment mechanism coupled to said covering and being configured to adjust said size of said covering, said size adjustment mechanism including
    a multi-layered electroactive polymer actuator including a first end and an opposite, second end, said first end of said multi-layered electroactive polymer actuator being coupled to said first portion of said covering, and
    a coupling member including a first end and an opposite, second end, said first end of said coupling member being coupled to said second end of said multi-layered electroactive polymer actuator, said second end of said coupling member being coupled to said second portion of said covering; said second end of said electroactive polymer actuator being oriented such that, upon actuation of said electroactive polymer actuator, said second end of said electroactive polymer actuator extends away from said first end of said electroactive polymer actuator to move said second portion of said covering towards said first portion of said covering.

12. The cardiac apparatus of claim 11, wherein said multi-layered electroactive polymer actuator includes a dielectric electrostrictive electroactive polymer.

13. The cardiac apparatus of claim 11, wherein said second end of said multi-layered electroactive polymer actuator is oriented such that, upon actuation of said multi-layered electroactive polymer actuator, said second end of said multi-layered electroactive polymer actuator extends away from said first end of said multi-layered electroactive polymer actuator to move said second portion of said covering towards said first portion of said covering.

14. The cardiac apparatus of claim 11, wherein said multi-layered electroactive polymer actuator defines an interior cavity, said coupling member extending through said interior cavity such that said first end of said coupling member is coupled to said second end of said multi-layered electroactive polymer actuator within said interior cavity.

15. The cardiac apparatus of claim 11, wherein said size adjustment mechanism further includes a releasable latch member coupled to said first portion of said covering and said second portion of said covering, said releasable latch member being configured to retain said first portion of said covering at a desired spacing with respect to said second portion of said covering.

16. The cardiac apparatus of claim 15, further comprising:
   a controller electrically coupled to said multi-layered electroactive polymer actuator, said controller being configured to actuate said multi-layered electroactive polymer actuator to allow gradual reshaping of said heart.

17. The cardiac apparatus of claim 11, further comprising:
   a sensor configured to detect a cardiac cycle of said heart; and
   a controller electrically coupled to said sensor and to said multi-layered electroactive polymer actuator, said controller being configured to actuate said multi-layered electroactive polymer actuator based on said cardiac cycle.

18. A cardiac apparatus comprising a covering configured to at least partially surround a heart; and a size adjustment mechanism coupled to said covering, said size adjustment mechanism including an electroactive polymer configured to expand upon actuation to compress said heart, wherein said covering includes a frame including a first support member and a second support member spaced apart from said first support member, said electroactive polymer actuator being formed as a film extending between said first support member and said second support member and being configured to expand inwardly upon actuation to compress said heart.

19. The cardiac apparatus of claim 18, wherein said covering includes a first portion and a second portion, said covering being configured to at least partially encircle said heart with said first portion of said covering adjacent to said second portion of said covering, said size adjustment mechanism further comprising a coupling member including a first end and a second end, said electroactive polymer actuator including a first end and a second end, said first end of said electroactive polymer actuator being coupled to said first portion of said covering and said first end of said coupling member being coupled to said second end of said electroactive polymer actuator and said second end of said coupling member being coupled to said second portion of said covering, said second end of said electroactive polymer actuator being oriented such that, upon actuation of said electroactive polymer actuator, said second end of said electroactive polymer actuator extends away from said first end of said electroactive polymer actuator to move said second portion of said covering towards said first portion of said covering.

20. The cardiac apparatus of claim 19, wherein said size adjustment mechanism further includes a coupling member including a first end and a second end, said first end of said coupling member being coupled to said second end of said electroactive polymer actuator, said second end of said coupling member being coupled to said second portion of said covering.

21. The cardiac apparatus of claim 19, wherein said size adjustment mechanism further includes a releasable latch member coupled to said first portion of said covering and said second portion of said covering, said releasable latch member being configured to retain said first portion of said covering at a desired spacing with respect to said second portion of said covering.

22. The cardiac apparatus of claim 21, further comprising:
   a controller electrically coupled to said electroactive polymer actuator, said controller being configured to actuate said electroactive polymer actuator to allow gradual reshaping of said heart.

* * * * *